United States Patent
Yoshinaga (10) Patent No.: US 10,525,444 B2
(45) Date of Patent: Jan. 7, 2020

(54) METHOD AND APPARATUS FOR MANUFACTURING WATER ABSORPTION TREATMENT MATERIAL

(71) Applicant: DAIKI CO., LTD., Tokyo (JP)

(72) Inventor: Junji Yoshinaga, Tokyo (JP)

(73) Assignee: DAIKI CO., LTD., Tokyo (JP)

( * ) Notice: Subject to any disclaimer, the term of this patent is extended or adjusted under 35 U.S.C. 154(b) by 0 days.

(21) Appl. No.: 16/108,553

(22) Filed: Aug. 22, 2018

(65) Prior Publication Data

US 2018/0353936 A1  Dec. 13, 2018

Related U.S. Application Data (63) Continuation of application No. PCT/JP2017/006499, filed on Feb. 22, 2017.

(30) Foreign Application Priority Data

Mar. 28, 2016 (JP) .................................. 2016-063612

(51) Int. Cl.
| | |
|---|---|
| *B01J 20/28* | (2006.01) |
| *B29C 48/04* | (2019.01) |
| *A01K 1/015* | (2006.01) |
| *B01J 20/30* | (2006.01) |
| *B01J 20/32* | (2006.01) |
| *A61L 15/20* | (2006.01) |
| *B01J 20/22* | (2006.01) |
| *B29B 9/12* | (2006.01) |
| *B29B 9/16* | (2006.01) |

(52) U.S. Cl.
CPC ....... *B01J 20/28016* (2013.01); *A01K 1/0155* (2013.01); *B01J 20/3007* (2013.01); *B01J 20/3028* (2013.01); *B01J 20/3293* (2013.01); *B29C 48/04* (2019.02); *A61L 15/20* (2013.01); *B01J 20/22* (2013.01); *B29B 9/12* (2013.01); *B29B 2009/163* (2013.01)

(58) Field of Classification Search
None
See application file for complete search history.

(56) References Cited

U.S. PATENT DOCUMENTS

| | | | | |
|---|---|---|---|---|
| 6,148,768 | A * | 11/2000 | Ochi | .................... A01K 1/0155 |
| | | | | 119/172 |
| 2016/0082416 | A1* | 3/2016 | Mochizuki | ........... A01K 1/0155 |
| | | | | 119/171 |

FOREIGN PATENT DOCUMENTS

JP  2007-190026 A  8/2007

* cited by examiner

*Primary Examiner* — Mary Lynn F Theisen
(74) *Attorney, Agent, or Firm* — Oliff PLC (57) ABSTRACT

A manufacturing apparatus is an apparatus for manufacturing a water absorption treatment material that is composed of a plurality of grains that bond to each other upon absorbing a liquid, and includes a granulation machine and a pressure application machine. The granulation machine forms a substantially cylindrical granule that constitutes each of the grains by granulating a granulation material. The pressure application machine applies pressure to the granule formed by the granulation machine from a longitudinal direction of the granule so as to reduce the length of the granule.

20 Claims, 8 Drawing Sheets

METHOD AND APPARATUS FOR MANUFACTURING WATER ABSORPTION TREATMENT MATERIAL

CROSS REFERENCE TO RELATED APPLICATION

This is a Continuation of International Application No. PCT/JP2017/006499 filed Feb. 22, 2017, which claims the benefit of Japanese Application No. 2016-063612 filed Mar. 28, 2016. The contents of these applications are hereby incorporated by reference in their entirety.

TECHNICAL FIELD

The present invention relates to a method and an apparatus for manufacturing a water absorption treatment material that absorbs a liquid.

BACKGROUND ART

A conventional water absorption treatment material is disclosed in Patent Document 1, for example. The water absorption treatment material disclosed in this document is composed of a plurality of grains that have water absorbing properties. The grains contain an adhesive material, and thus bond to each other upon absorbing a liquid when in use. As a result, a clump composed of a plurality of used grains is formed.

CITATION LIST

Patent Document

Patent Document 1: JP 2007-190026 A

SUMMARY OF INVENTION

Technical Problem

Because a clump of grains is formed as described above, used grains can be selectively removed with ease from the water absorption treatment material that contains unused grains and used grains in a mixed manner. However, there is still room for improvement in the conventional water absorption treatment material in terms of the clumping strength of grains.

Solution to Problem

The present invention has been made in view of the problem described above, and it is an object of the present invention to provide a method and an apparatus for manufacturing a water absorption treatment material in which used grains have excellent clumping strength.

A method for manufacturing a water absorption treatment material according to the present invention is a method for manufacturing a water absorption treatment material that is composed of a plurality of grains that bond to each other upon absorbing a liquid. The method includes: a granulation step of forming a substantially cylindrical granule that constitutes each of the grains by granulating a granulation material; and a pressure application step of applying pressure to the granule formed in the granulation step from a longitudinal direction of the granule so as to reduce a length of the granule.

The manufacturing method includes the pressure application step. In the pressure application step, the length of the substantially cylindrical granule is reduced. In the case of a cylindrical granule, the proportion of the surface area to the volume of the granule increases as the length of the granule decreases. When the surface area is increased as described above, the contact area between the grains also increases. For this reason, in the manufactured water absorption treatment material, strong adhesion between adjacent grains can be obtained.

Also, an apparatus for manufacturing a water absorption treatment material according to the present invention is an apparatus for manufacturing a water absorption treatment material that is composed of a plurality of grains that bond to each other upon absorbing a liquid. The apparatus includes: a granulation machine that forms a substantially cylindrical granule that constitutes each of the grains by granulating a granulation material; and a pressure application machine that applies pressure to the granule formed by the granulation machine from a longitudinal direction of the granule so as to reduce a length of the granule.

The manufacturing apparatus includes the pressure application machine. In the pressure application machine, the length of the substantially cylindrical granule is reduced. In the case of a cylindrical granule, the proportion of the surface area to the volume of the granule increases as the length of the granule decreases. When the surface area is increased as described above, the contact area between the grains also increases. For this reason, in the manufactured water absorption treatment material, strong adhesion between adjacent grains can be obtained.

Advantageous Effects of Invention

According to the present invention, it is possible to implement a method and an apparatus for manufacturing a water absorption treatment material in which used grains have excellent clumping strength.

DESCRIPTION OF EMBODIMENTS

Hereinafter, an embodiment of the present invention will be described in detail with reference to the drawings. In the description of the drawings, the same elements are given the same reference numerals, and a redundant description will be omitted.

Figure 1:
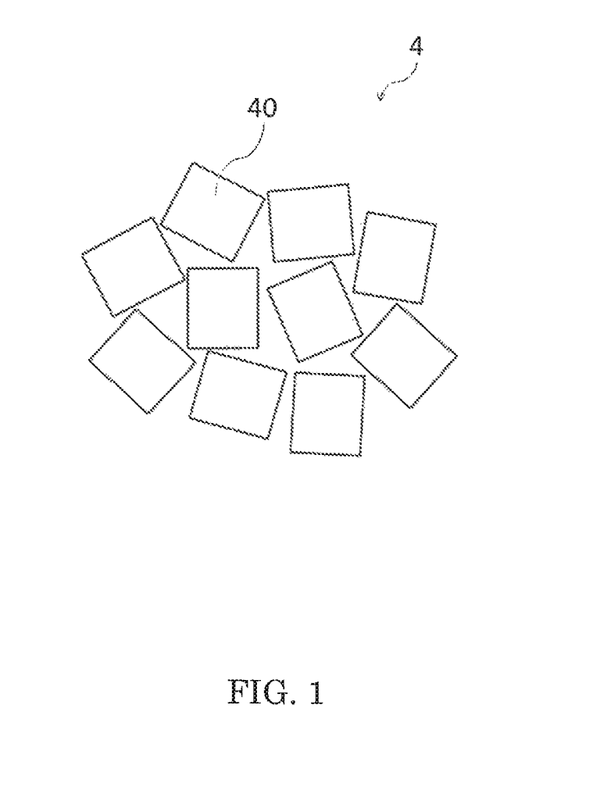
FIG. 1 is a schematic diagram showing a water absorption treatment material according to an embodiment of the present invention.

FIG. 1 is a schematic diagram showing a water absorption treatment material according to an embodiment of the present invention. A water absorption treatment material 4 is composed of a plurality of grains 40. Each grain 40 has water absorbing properties, and absorbs a liquid for disposal. The grains 40 are configured so as to bond to each other upon absorbing a liquid. The water absorption treatment material 4 is used as, for example, an excrement treatment material that absorbs human or animal excrement for disposal.

Figure 2:
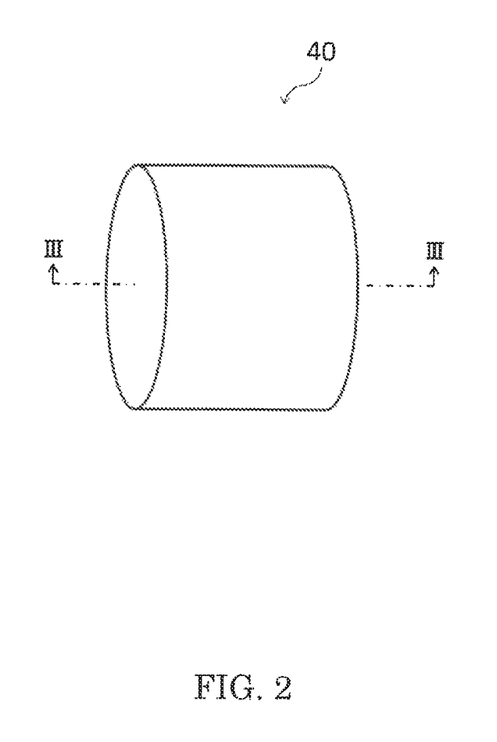
FIG. 2 is a perspective view of a grain 40.
Figure 3:
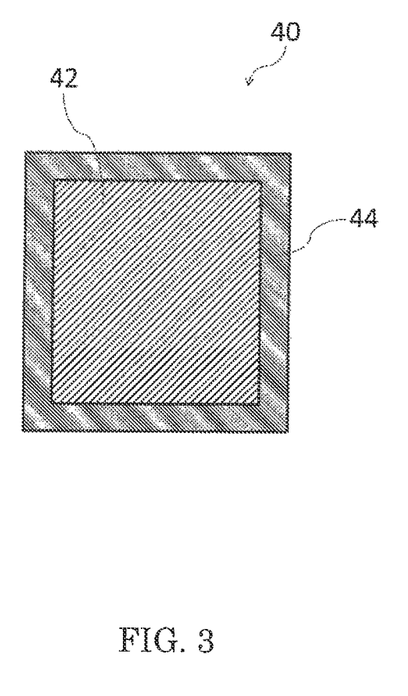
FIG. 3 is a cross-sectional view taken along the line III-III shown in FIG. 2.

FIG. 2 is a perspective view of the grain 40. FIG. 3 is a cross-sectional view taken along the line III-III shown in FIG. 2. The grain 40 has a substantially cylindrical shape. The grain 40 includes a core portion 42 (granule) and a coating portion 44.

Figure 4:
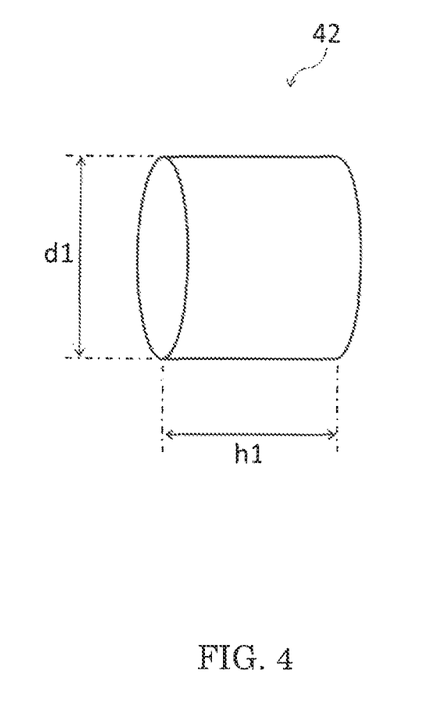
FIG. 4 is a perspective view of a core portion 42.

FIG. 4 is a perspective view of the core portion 42. The core portion 42 has a substantially cylindrical shape. The core portion 42 preferably has a length h1 that is less than or equal to the diameter d1 of the core portion 42, and more preferably a length h1 that is 60% or more and 80% or less of the diameter d1. Each end (a portion corresponding to the bottom of a cylinder) of the core portion 42 may have irregularities. Accordingly, the length of the core portion 42 as used herein refers to a distance between the highest points of two opposing end portions. Specifically, a distance between two planes that are perpendicular to the longitudinal direction of the core portion 42 and are disposed such that one of the planes abuts against at least a portion of one end of the core portion 42 and the other plane abuts against at least a portion of the other end of the core portion 42, is defined as the length of the core portion 42.

The core portion 42 has a function of absorbing and retaining a liquid. The core portion 42 preferably contains an organic substance as the main material. As used herein, the main material of the core portion 42 refers to one of the materials constituting the core portion 42 that accounts for the highest proportion by weight in the core portion 42. It is possible to use, for example, papers, used tea leaves, plastics, or soybean refuse as the organic substance.

Papers refer to a material composed mainly of pulp. Examples of papers include ordinary paper, a vinyl chloride wallpaper classified product (paper obtained by classifying vinyl chloride wallpaper), a fluff pulp, a papermaking sludge, a pulp sludge, and the like. As the plastics, it is possible to use, for example, a disposable diaper classified product (plastics obtained by classifying disposable diapers). The soybean refuse is preferably dried soybean refuse.

Referring back to FIG. 3, the coating portion 44 covers the core portion 42. The coating portion 44 has a function of bonding grains 40 that have absorbed a liquid when in use, and forming them into a clump. The coating portion 44 also preferably contains an organic substance as the main material. The coating portion 44 contains an adhesive material. As the adhesive material, it is possible to use, for example, starch, CMC (carboxymethyl cellulose), PVA (polyvinyl alcohol), dextrin, or a water-absorbent polymer.

Figure 5:
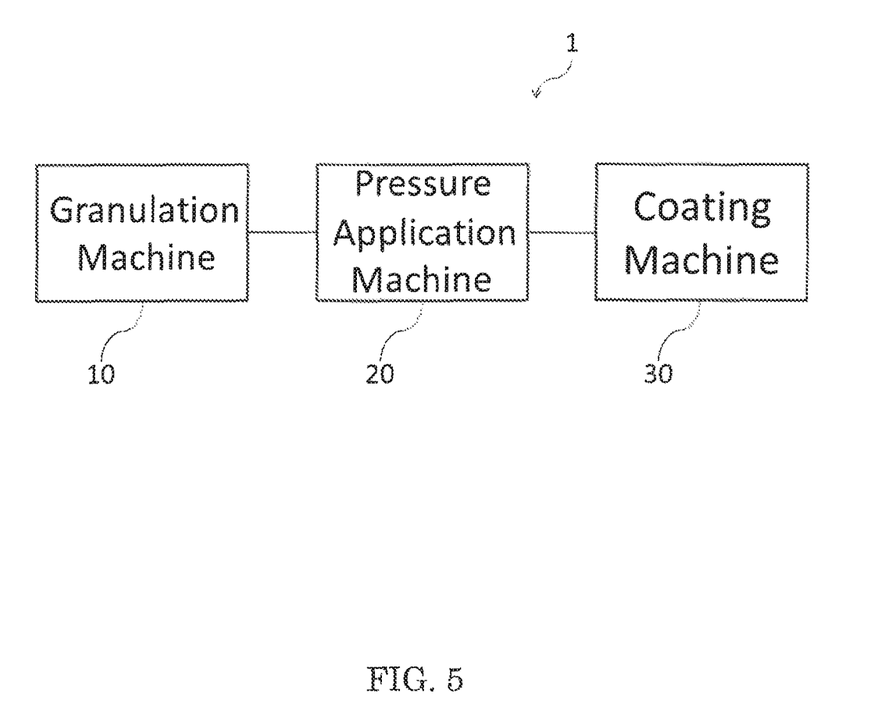
FIG. 5 is a configuration diagram of an apparatus for manufacturing a water absorption treatment material according to an embodiment of the present invention.

FIG. 5 is a configuration diagram of an apparatus for manufacturing a water absorption treatment material according to an embodiment of the present invention. A manufacturing apparatus 1 is an apparatus for manufacturing the above-described water absorption treatment material 4. The manufacturing apparatus 1 includes a granulation machine 10, a pressure application machine 20, and a coating machine 30.

The granulation machine 10 is a machine for forming granules that each have a substantially cylindrical shape and will serve as the core portion 42 by granulating a granulation material (a material for forming the core portions 42). In the granulation machine 10, it is preferable that granules that each have a length that is larger than the diameter thereof are formed. In the present embodiment, the granulation machine 10 is an extrusion granulation machine. The extrusion granulation machine includes a die and a cutter. In the die, a plurality of through holes that allow the granulation material to pass therethrough are formed. The through holes have a circular shape when viewed in a plan view. In the extrusion granulation machine, the granulation material that has been extruded from the through holes of the die is cut by the cutter, and thereby a plurality of granules are obtained.

Figure 6:
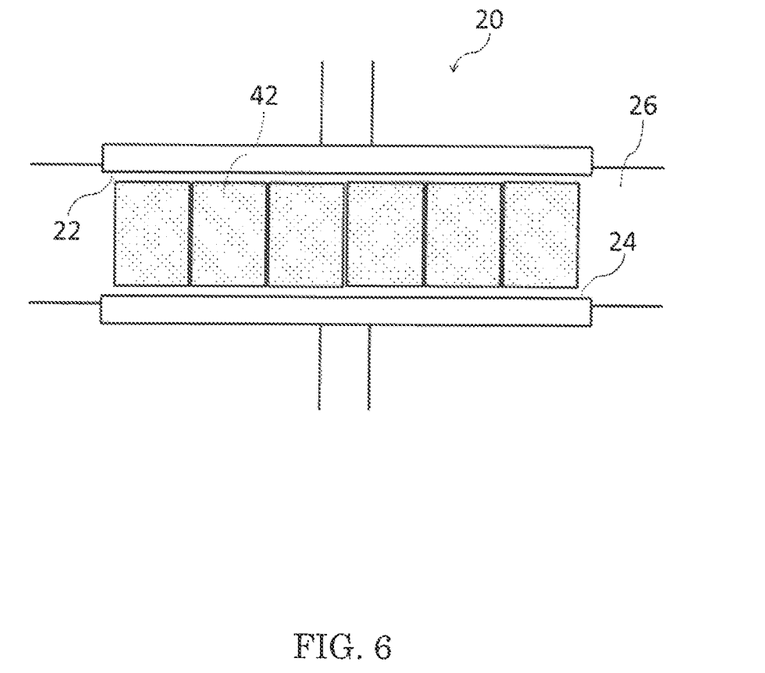
FIG. 6 is a plan view of a pressure application machine 20.

FIG. 6 is a plan view of the pressure application machine 20. The pressure application machine 20 is a machine that applies pressure to each of the granules formed by the granulation machine 10 from a longitudinal direction of the granule so as to reduce the length of the granule. In the present embodiment, the application of pressure by the pressure application machine 20 is performed prior to the coating portion 44 being formed by the coating machine 30, which will be described later.

The pressure application machine 20 includes a pressure application surface 22 (first pressure application surface), a pressure application surface 24 (second pressure application surface), and a placement surface 26. The pressure application surface 22 and the pressure application surface 24 are provided opposing each other. In the present embodiment, the pressure application surfaces 22 and 24 are flat surfaces that are parallel to each other. Each of the pressure application surfaces 22 and 24 is movable in a direction perpendicular to the pressure application surface (in the up-down direction in FIG. 6). That is, the distance between the pressure application surface 22 and the pressure application surface 24 is variable. A granule (core portion 42) is placed on the placement surface 26. The core portion 42 is placed such that the longitudinal direction of the core portion 42 is perpendicular to the pressure application surfaces 22 and 24. FIG. 6 shows a state in which a plurality of core portions 42 are placed on the placement surface 26.

Figure 7:
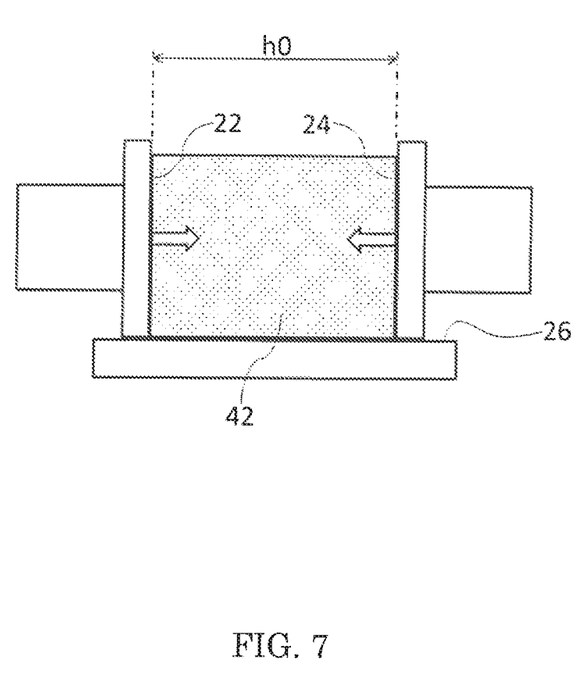
FIG. 7 is a side view illustrating an operation of the pressure application machine 20.
Figure 8:
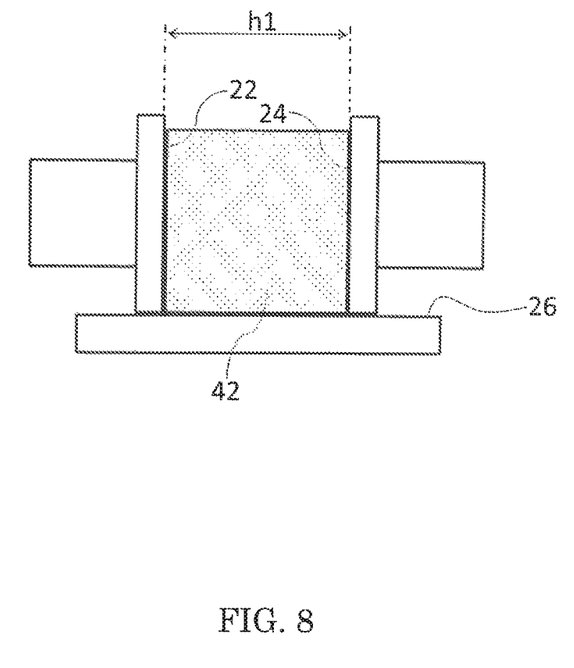
FIG. 8 is a side view illustrating an operation of the pressure application machine 20.

As shown in FIGS. 7 and 8, the pressure application machine 20 applies pressure to the core portion 42 by moving the pressure application surface 24 closer to the pressure application surface 22 in a state in which the first end of the core portion 42 is in abutment with the pressure application surface 22, and the second end of the core portion 42 is in abutment with the pressure application surface 24. In particular, in the present embodiment, pressure is applied simultaneously to a plurality of core portions 42 by moving the pressure application surface 24 closer to the pressure application surface 22 in a state in which the first ends of the plurality of core portions 42 are in abutment with the pressure application surface 22, and the second ends of the plurality of core portions 42 are in abutment with the pressure application surface 24. The pressed core portions 42 are compressed in the longitudinal direction, and the length of the pressed core portions 42 is reduced. That is, the length h1 of the core portion 42 immediately after pressure is applied (see FIG. 8) is smaller than the length h0 of the core portion 42 immediately before the pressure is applied (see FIG. 7).

The length h1 is preferably 90% or less of the length h0, and more preferably 80% or less of the length h0. That is, the pressure application machine 20 preferably reduces the length of the core portion 42 by 10% or more, and more preferably reduces the length of the core portion 42 by 20% or more. Also, the pressure application machine 20 preferably reduces the length of the core portion 42 such that the length h1 is less than or equal to the diameter d1 (see FIG.

4), and more preferably reduces the length of the core portion 42 such that the length h1 is 60% or more and 80% or less of the diameter d1.

Referring back to FIG. 5, the coating machine 30 is a machine for forming the coating portion 44 that covers the core portion 42 formed by the granulation machine 10. The coating machine 30 forms the coating portion 44 by attaching a powdered coating material (a material for forming the coating portions 44) to the surface of each core portion 42. The attachment of the coating material may be performed by, for example, sprinkling or spraying the coating material.

Next, a method for manufacturing a water absorption treatment material according to an embodiment of the present invention will be described in conjunction with the operations of the manufacturing apparatus 1. The manufacturing method includes a granulation step, a pressure application step, and a coating step. The granulation step is a step of forming substantially cylindrical granules that will each serve as the core portion 42 by granulating a granulation material using the granulation machine 10. In the granulation step, it is preferable that granules that each have a length that is larger than the diameter of the granule are formed. Prior to granulation, the granulation material is subjected to pre-treatment such as pulverization, kneading, and adding water, as needed.

The pressure application step is a step of applying pressure to each of the granules formed by the granulation machine 10 from the longitudinal direction of the granule so as to reduce the length of the granule. In the present embodiment, the pressure application step is performed prior to the coating step, which will be described later. In the pressure application step, using the pressure application machine 20 described above, pressure is applied to the core portions 42 by moving the pressure application surface 24 closer to the pressure application surface 22 in a state in which the first ends of the core portions 42 are in abutment with the pressure application surface 22, and the second ends of the core portions 42 are in abutment with the pressure application surface 24. As a result, the length of the core portions 42 is reduced.

In the pressure application step, it is preferable to reduce the length of the core portions 42 by 10% or more, and it is more preferable to reduce the length of the core portions 42 by 20% or more. Also, in the pressure application step, it is preferable to reduce the length of the core portions 42 such that the length h1 immediately after pressure is applied is less than or equal to the diameter d1, and it is more preferable to reduce the length of the core portions 42 such that the length h1 is 60% or more and 80% or less of the diameter d1.

The coating step is a step of forming the coating portion 44 that covers the core portion 42 formed in the granulation step. In the present embodiment, the coating portion 44 is formed on the core portion 42 that has been pressed in the pressure application step. In the coating step, by using the coating machine 30 described above, the coating portion 44 is formed by attaching a coating material to the surface of each core portion 42. Then, post-treatment such as sieving (sizing) and drying is performed as needed. Through the above processing, the water absorption treatment material 4 composed of the plurality of grains 40 is obtained.

Advantageous effects of the present embodiment will be described. In the present embodiment, pressure is applied to the granule (core portion 42), and the length of the granule is thereby reduced. In the case of a cylindrical granule, the proportion of the surface area to the volume of the granule increases as the length of the granule decreases. When the surface area is increased as described above, the contact area between the grains 40 also increases. For this reason, in the water absorption treatment material 4, strong adhesion between adjacent grains 40 can be obtained. Accordingly, it is possible to implement a method and an apparatus for manufacturing the water absorption treatment material 4 in which used grains 40 have excellent clumping strength.

As a means for obtaining granules that have a small (short) length, forming short granules directly in the granulation step can be of course considered. However, forming short granules at the stage of granulation may cause a problem such as a reduction in yield. According to the present embodiment, the length of the granules is adjusted after granulation, and thus even if relatively long granules are formed at the stage of granulation, it is possible to ultimately obtain short grains.

In this regard, in a conventional water absorption treatment material, it is common to use granules that have a length that is larger than their diameter. In view of this, it is preferable that, in the granulation step, core portions 42 that each have a length that is larger than the diameter thereof are formed, and in the pressure application step, the length of the core portions 42 is adjusted to be less than or equal to the diameter thereof. In doing so, it is possible to improve the clumping strength of the grains 40 while avoiding a problem such as a reduction in yield.

As described above, in order to ultimately obtain short core portions 42 while forming relatively long core portions 42 at the stage of granulation, it is preferable to sufficiently reduce the length of the core portions 42 at the stage of application of pressure. From this viewpoint, in the pressure application step, the length of the core portions 42 is reduced preferably by 10% or more, and more preferably by 20% or more.

In the case of a cylinder that is inscribed in a sphere, the cylinder is at its maximum volume when the length (height) of the cylinder is about 70% of the diameter of the cylinder. Accordingly, when the length h1 of the core portion 42 is around 70% of the diameter d1, the core portion 42 has a shape relatively close to a sphere. In this case, a plurality of grains 40 can be placed at a high density in the water absorption treatment material 4, and thus gaps between adjacent grains 40 become small. This also contributes to an improvement in the clumping strength of the grains 40. From this viewpoint, in the pressure application step, it is preferable to reduce the length of the core portion 42 such that the length of the core portion 42 is 60% or more and 80% or less of the diameter d1.

In the pressure application step, by using the pressure application machine 20, pressure is applied to the core portion 42 by moving the pressure application surface 24 closer to the pressure application surface 22 in a state in which the first end of the core portion 42 is in abutment with the pressure application surface 22, and the second end of the core portion 42 is in abutment with the pressure application surface 24. In doing so, it is possible to apply pressure to the core portion 42 from a longitudinal direction of the core portion 42 with a simple configuration. Also, the length of the core portion 42 immediately after pressure is applied can be defined by the distance between the pressure application surface 22 and the pressure application surface 24. Accordingly, there is also an advantage in that the core portion 42 with a desired length can be easily obtained.

In particular, in the present embodiment, pressure is applied simultaneously to the plurality of core portions 42 in a state in which the first ends of the plurality of core portions 42 are in abutment with the pressure application surface 22, and the second ends of the plurality of core portions 42 are in abutment with the pressure application surface 24. In doing so, it is possible to simultaneously reduce the length of the plurality of core portions 42. Also, it is possible to obtain the plurality of core portions 42 that have little variation in length.

The pressure application step is performed prior to the coating step. That is, pressure is applied to the core portions 42 before the coating portions 44 are formed on the core portions 42. In this case, it is possible to reliably avoid a situation in which the coating portions 44 are separated from the core portions 42 due to the application of pressure.

In the granulation step, granules are formed using an extrusion granulation machine. Accordingly, it is possible to easily obtain granules formed in a substantially cylindrical shape.

In the case where the core portion 42 and the coating portion 44 contain an organic substance as the main material, it is possible to obtain the grain 40 suitable for being disposed of through incineration. In this case, a clump of used grains 40 can be discarded as combustible trash, and it is therefore possible to improve convenience for a user.

The present invention is not limited to the embodiment given above, and various modifications can be made. In the embodiment given above, an example has been described in which the pressure application step is performed prior to the coating step. However, the pressure application step may be performed after the coating step. In this case, in the pressure application machine 20, pressure is applied to the core portion 42 by moving the pressure application surface 24 closer to the pressure application surface 22 in a state in which the first end of the core portion 42 is in abutment with the pressure application surface 22 via the coating portion 44 and the second end of the core portion 42 is in abutment with the pressure application surface 24 via the coating portion 44.

In the embodiment given above, an example has been described in which the pressure application surface 22 and the pressure application surface 24 are both movable. However, a configuration is possible in which either one of the pressure application surface 22 and the pressure application surface 24 is movable, and the other pressure application surface is fixed.

In the embodiment given above, as an example of the configuration of the pressure application machine 20, the pressure application machine 20 that includes the pressure application surface 22 and the pressure application surface 24 has been described (see FIG. 6). However, the pressure application machine 20 may have a different configuration as long as it is possible to apply pressure to a granule from a longitudinal direction of the granule, and reduce the length of the granule. Also, the pressure application step does not require the use of the pressure application machine 20. For example, the first end of a granule may be pressed against a wall surface or another granule so as to apply pressure from a longitudinal direction of the granule. Alternatively, two opposing ends of a granule may be compressed between fingers so as to apply pressure from the longitudinal direction of the granule.

In the embodiment given above, an example has been described in which each grain 40 has a multi-layer structure composed of the core portion 42 and the coating portion 44. However, providing the coating portion 44 is not a requirement. That is, each grain 40 may have a single-layer structure composed only of the core portion 42. In this case, it is unnecessary to provide the coating machine 30, and the coating step is not performed. Even when the coating portion 44 is not provided, with the inclusion of an adhesive material in the core portion 42, it is possible to obtain a plurality of grains 40 that bond to each other upon absorbing a liquid.

LIST OF REFERENCE NUMERALS

1 Manufacturing Apparatus
4 Water Absorption Treatment Material
10 Granulation Machine
20 Pressure Application Machine
22 Pressure Application Surface (First Pressure Application Surface)
24 Pressure Application Surface (Second Pressure Application Surface)
26 Placement Surface
30 Coating Machine
40 Grain
42 Core Portion (Granule)
44 Coating Portion

The invention claimed is:

1. A method for manufacturing a water absorption treatment material that is composed of a plurality of grains that bond to each other upon absorbing a liquid, the method comprising:
   a granulation step of forming a substantially cylindrical granule that constitutes each of the grains by granulating a granulation material; and
   a pressure application step of applying pressure to the granule formed in the granulation step from a longitudinal direction of the granule so as to reduce a length of the granule.

2. The method for manufacturing a water absorption treatment material according to claim 1,
   wherein, in the granulation step, the granule is formed using an extrusion granulation machine.

3. The method for manufacturing a water absorption treatment material according to claim 1,
   wherein, in the pressure application step, the length of the granule is reduced by 10% or more.

4. The method for manufacturing a water absorption treatment material according to claim 3,
   wherein, in the pressure application step, the length of the granule is reduced by 20% or more.

5. The method for manufacturing a water absorption treatment material according to claim 1,
   wherein, in the granulation step, the granule that has a length that is larger than a diameter of the granule is formed, and
   in the pressure application step, the length of the granule is reduced such that the length of the granule is less than or equal to the diameter of the granule.

6. The method for manufacturing a water absorption treatment material according to claim 1,
   wherein, in the pressure application step, the length of the granule is reduced such that the length of the granule is 60% or more and 80% or less of a diameter of the granule.

7. The method for manufacturing a water absorption treatment material according to claim 1,
   wherein, in the pressure application step, by using a pressure application machine that includes mutually opposing first and second pressure application surfaces, the pressure is applied to the granule by moving the second pressure application surface closer to the first pressure application surface in a state in which a first end of the granule is in abutment with the first pressure application surface, and a second end of the granule is in abutment with the second pressure application surface.

8. The method for manufacturing a water absorption treatment material according to claim 7,
wherein, in the pressure application step, the pressure is applied simultaneously to a plurality of the granules by moving the second pressure application surface closer to the first pressure application surface in a state in which the first ends of the plurality of the granules are in abutment with the first pressure application surface, and the second ends of the plurality of the granules are in abutment with the second pressure application surface.

9. The method for manufacturing a water absorption treatment material according to claim 1, the method comprising:
a coating step of forming a coating portion so as to cover the granule formed in the granulation step.

10. The method for manufacturing a water absorption treatment material according to claim 9,
wherein the pressure application step is performed prior to the coating step.

11. An apparatus for manufacturing a water absorption treatment material that is composed of a plurality of grains that bond to each other upon absorbing a liquid, the apparatus comprising:
a granulation machine that forms a substantially cylindrical granule that constitutes each of the grains by granulating a granulation material; and
a pressure application machine that applies pressure to the granule formed by the granulation machine from a longitudinal direction of the granule so as to reduce a length of the granule.

12. The apparatus for manufacturing a water absorption treatment material according to claim 11,
wherein the granulation machine is an extrusion granulation machine.

13. The apparatus for manufacturing a water absorption treatment material according to claim 11,
wherein the pressure application machine reduces the length of the granule by 10% or more.

14. The apparatus for manufacturing a water absorption treatment material according to claim 13,
wherein the pressure application machine reduces the length of the granule by 20% or more.

15. The apparatus for manufacturing a water absorption treatment material according to claim 11,
wherein the granulation machine forms the granule that has a length that is greater than a diameter of the granule, and
the pressure application machine reduces the length of the granule such that the length of the granule is less than or equal to the diameter of the granule.

16. The apparatus for manufacturing a water absorption treatment material according to claim 11,
wherein the pressure application machine reduces the length of the granule such that the length of the granule is 60% or more and 80% or less of a diameter of the granule.

17. The apparatus for manufacturing a water absorption treatment material according to claim 11,
wherein the pressure application machine includes mutually opposing first and second pressure application surfaces, and applies the pressure to the granule by moving the second pressure application surface closer to the first pressure application surface in a state in which a first end of the granule is in abutment with the first pressure application surface, and a second end of the granule is in abutment with the second pressure application surface.

18. The apparatus for manufacturing a water absorption treatment material according to claim 17,
wherein the pressure application machine applies the pressure simultaneously to a plurality of the granules by moving the second pressure application surface closer to the first pressure application surface in a state in which the first ends of the plurality of the granules are in abutment with the first pressure application surface, and the second ends of the plurality of the granules are in abutment with the second pressure application surface.

19. The apparatus for manufacturing a water absorption treatment material according to claim 11, the apparatus comprising:
a coating machine that forms a coating portion so as to cover the granule formed by the granulation machine.

20. The apparatus for manufacturing a water absorption treatment material according to claim 19,
wherein the application of the pressure by the pressure application machine is performed prior to the formation of the coating portion by the coating machine.

* * * * *